(12) United States Patent
Qian et al.

(10) Patent No.: US 11,744,652 B2
(45) Date of Patent: Sep. 5, 2023

(54) VISUALIZATION OF PREDICTED DOSAGE

(71) Applicant: Medivis, Inc., New York, NY (US)

(72) Inventors: Long Qian, Brooklyn, NY (US); Christopher Morley, New York, NY (US); Osamah Choudhry, New York, NY (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 17/871,885

(22) Filed: Jul. 22, 2022

(65) Prior Publication Data

US 2022/0354591 A1  Nov. 10, 2022

Related U.S. Application Data

(63) Continuation-in-part of application No. 17/502,030, filed on Oct. 14, 2021, and a continuation-in-part of application No. 17/395,233, filed on Aug. 5, 2021, said application No. 17/502,030 is a continuation of application No. 17/148,522, filed on Jan. 13, 2021, now Pat. No. 11,172,996.

(51) Int. Cl.
*A61B 34/20* (2016.01)
*G06T 19/00* (2011.01)
*A61B 34/00* (2016.01)
*G06T 19/20* (2011.01)

(52) U.S. Cl.
CPC .............. *A61B 34/20* (2016.02); *A61B 34/25* (2016.02); *G06T 19/006* (2013.01); *G06T 19/20* (2013.01); *A61B 2034/2068* (2016.02)

(58) Field of Classification Search
None
See application file for complete search history.

(56) References Cited

U.S. PATENT DOCUMENTS

| | | | |
|---|---|---|---|
| 7,427,272 | B2 | 9/2008 | Richard et al. |
| 2008/0228064 | A1 | 9/2008 | Krueger et al. |
| 2010/0002921 | A1 | 1/2010 | Fenchel |
| 2013/0113802 | A1* | 5/2013 | Weersink ............... G06T 19/00 345/427 |
| 2014/0171787 | A1 | 6/2014 | Garbey et al. |
| 2015/0265367 | A1 | 9/2015 | Gruhler |
| 2018/0063386 | A1* | 3/2018 | Sharma ................ H04N 5/232 |
| 2018/0193097 | A1 | 7/2018 | Mclachlin et al. |
| 2018/0253856 | A1 | 9/2018 | Price et al. |
| 2018/0272153 | A1* | 9/2018 | Berlinger ............ A61N 5/1075 |

(Continued)

*Primary Examiner* — Patricia J Park
(74) *Attorney, Agent, or Firm* — Cognition IP, P.C.; Edward Steakley; Rajsh Fotedar (57) ABSTRACT

Various embodiments of an apparatus, methods, systems and computer program products described herein are directed to Field Visualization Engine. The Field Visualization Engine tracks one or more collimator poses relative to one or more Augmented Reality (AR) headset device poses. Each respective collimator pose and each respective headset device pose corresponds to a three-dimensional (3D) unified coordinate space ("3D space"). The Field Visualization Engine generates an AR representation of a beam emanating from the collimator based at least on a current collimator pose and a current headset device pose. The Field Visualization Engine further generates an AR visualization of emanation of the beam throughout an AR display of medical data.

11 Claims, 9 Drawing Sheets

(56) References Cited

U.S. PATENT DOCUMENTS

| | | |
|---|---|---|
| 2019/0090955 A1 | 3/2019 | Singh et al. |
| 2019/0311490 A1* | 10/2019 | Crawford ................ G06F 3/011 |
| 2020/0005486 A1 | 1/2020 | Sinha et al. |
| 2020/0197107 A1* | 6/2020 | Ryan ...................... A61B 90/98 |
| 2020/0352655 A1 | 11/2020 | Freese |
| 2021/0038181 A1* | 2/2021 | Schweizer ............ A61B 6/466 |
| 2021/0169581 A1* | 6/2021 | Calloway ............... A61B 34/74 |
| 2021/0378756 A1 | 12/2021 | Calloway et al. |

\* cited by examiner

VISUALIZATION OF PREDICTED DOSAGE

CROSS-REFERENCE TO RELATED APPLICATIONS

This application is a continuation-in-part of U.S. patent application Ser. No. 17/395,233, filed on Aug. 5, 2021, titled "MEDICAL INSTRUMENT WITH FIDUCIAL MARKERS," which claims priority to U.S. patent application Ser. No. 17/148,522 (now U.S. Pat. No. 11,172,996), the entirety of which is incorporated herein by reference.

This application is a continuation-in-part of U.S. patent application Ser. No. 17/502,030, filed on Oct. 14, 2021, titled "INSTRUMENT-BASED REGISTRATION AND ALIGNMENT FOR AUGMENTED REALITY ENVIRONMENTS," which also claims priority to U.S. patent application Ser. No. 17/148,522 (now U.S. Pat. No. 11,172,996), the entirety of which is incorporated herein by reference.

BACKGROUND

Current conventional systems have limitations with regard to two-dimensional (2D) and three-dimensional (3D) images in surgical settings. Surgical planning is necessary for every medical procedure. A surgeon and their team must have a plan for a case before entering an operating room, not just as a matter of good practice but to minimize malpractice liabilities and to enhance patient outcomes. Surgical planning is often conducted based on medical images including DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

SUMMARY

Various embodiments of an apparatus, methods, systems and computer program products described herein are directed to a Field Visualization Engine. Various embodiments are described herein as including an external instrument comprising a collimator. It is understood that external instruments of various embodiments of the Field Visualization Engine are not limited solely to a collimator. That is, embodiments of the Field Visualization Engine may substitute the collimator for any module that generates and transmits an energy beam or electric field (such as a magnetic field). For example, embodiments described herein include any type of external instrument that provides some form of treatment (or performs some type of diagnosis) of a patient.

According to various embodiments, the Field Visualization Engine tracks one or more positions and orientations of a collimator ("collimator poses") relative to one or more positions and orientations of an Augmented Reality (AR) headset device ("headset poses" or "device poses") worn by a user. Each respective collimator pose and each respective headset pose corresponds to a three-dimensional (3D) unified coordinate space ("3D space"). The Field Visualization Engine generates an AR representation of a beam (such as a radiation beam) emanating from the collimator based at least on a current collimator pose and a current headset pose. The Field Visualization Engine further generates an AR visualization of emanation of the beam throughout an AR display of medical data.

According to various embodiments, AR visualization of emanation of the beam may be based on a simulated beam (such as a simulated radiation beam) or may be a real-time AR visualization of an actual beam currently being delivered by the collimator.

In various embodiments, a user may wear an AR headset device as part of a component of the Field Visualization Engine. The AR headset device generates an AR display that includes 3D medical model data displayed as an overlay over a physical patient. The 3D medical model data may be representative of a portion of the physical patient's anatomy. As the user continually moves and the headset pose continually changes, the Field Visualization Engine captures the current headset pose and retrieves medical model data that corresponds with the user's perspective view. The Field Visualization Engine continually updates the overlay by rendering newly retrieved medical model data.

In various embodiments, the Field Visualization Engine incorporates mask layers into the AR display of the 3D medical model data. The mask layers provide a preview of how a sphere of a planned dose of radiation may emanate throughout the patient's internal anatomy and also provides a visual indication of predicted radiation fall off.

In various embodiments, the Field Visualization Engine determines the collimator pose for a collimator physically positioned proximate to the patient. The AR headset further generates an AR visualization of a simulated radiation beam generated by the collimator and targeted at the patient.

In one or more embodiments, the AR headset device displays the AR visualization of a simulated radiation beam relative to a current headset pose. The AR visualization of a simulated radiation beam represents a view of the simulated radiation beam from the user's current perspective view as the user moves and the headset pose continually changes.

In various embodiments, the AR display includes concurrent display of the medical model data overlay with mask layers and the AR visualization of the simulated radiation beam.

According to one or more embodiments, the Field Visualization Engine determines predicted interactions between the simulated radiation beam and the various types of targeted tissue, muscle and/or organs of the patient's internal anatomy represented by the medical model data.

In one or more embodiments, the AR headset device incorporates visual indications in the medical model data overlay to provide a visualization of how the simulated radiation beam may emanate throughout the internal anatomy, the fall off of the simulated radiation beam and the effects the internal anatomy may experience as a consequence of exposure to the simulated radiation beam.

In some embodiments, the Field Visualization Engine triggers display of a visual cue upon determining the emanation of the simulated radiation beam and fall off that corresponds with the collimator's current pose is in alignment with the emanation of the planned dose of radiation and its fall off.

According to various embodiments, the Field Visualization Engine (or a portion of the Field Visualization Engine) may be implemented in an external computer device(s) to track the collimator poses and the headset poses.

Various embodiments include a module(s) and/or one or more functionalities to redact privacy information/data (such as medical data), to encrypt information/data and to anonymize data to ensure the confidentiality and security of user, patient and system information/data as well as compliance with medical regulatory and privacy law(s) in the United State and/or international jurisdictions.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

Figure 1A:
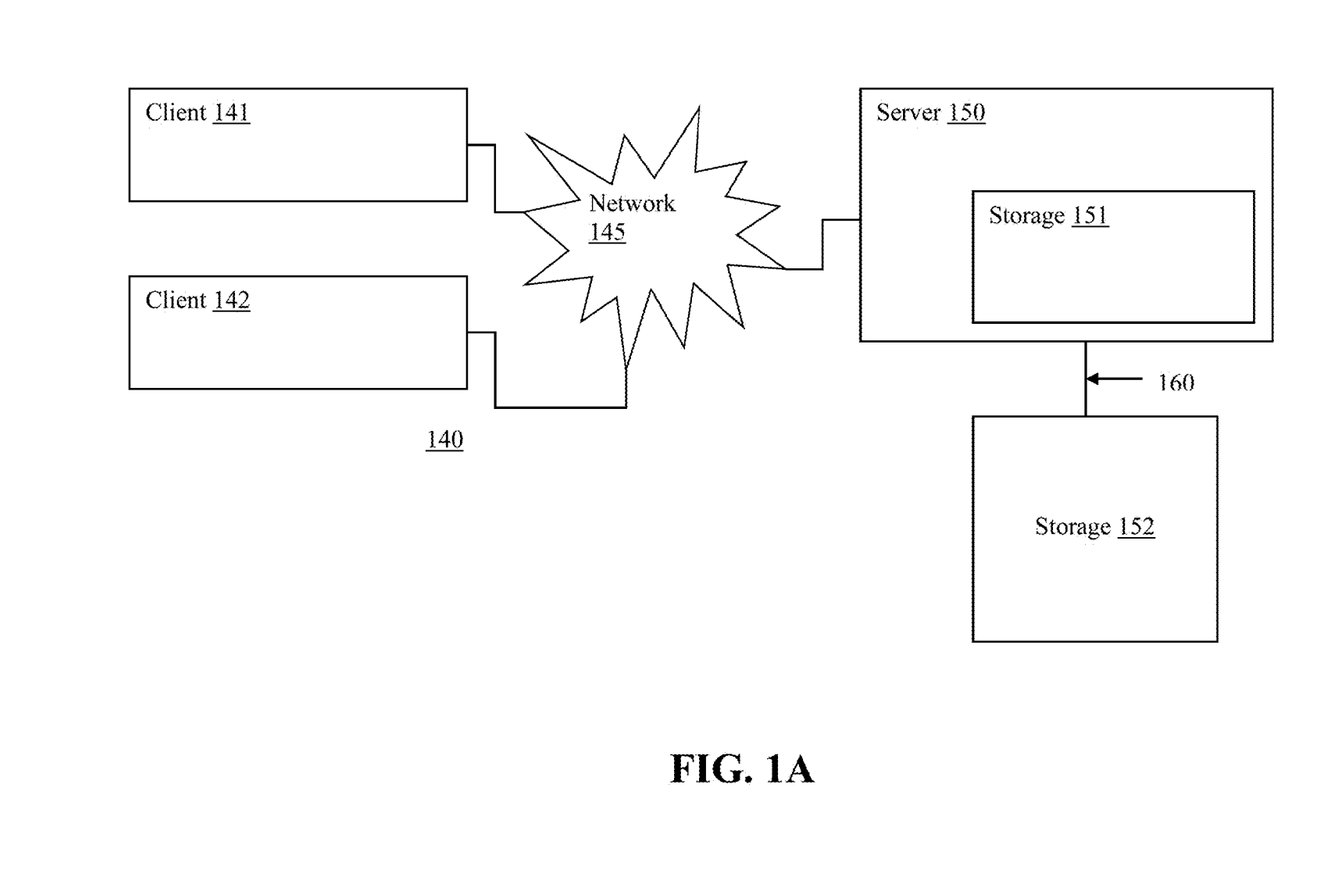
FIG. 1A is a diagram illustrating an exemplary environment in which some embodiments may operate.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

Figure 2:
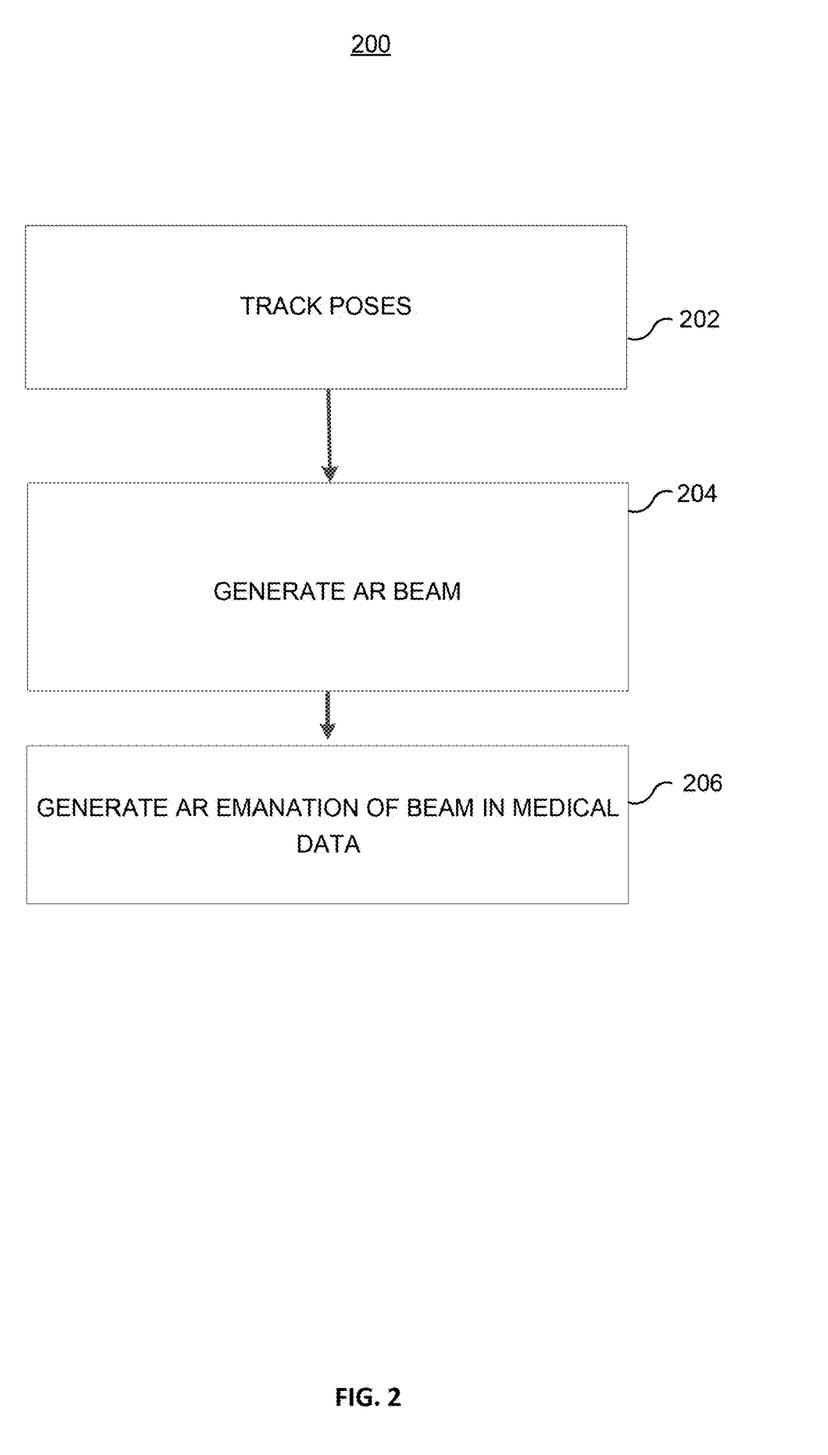
FIG. 2 is a diagram illustrating an exemplary method that may be performed in some embodiments.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
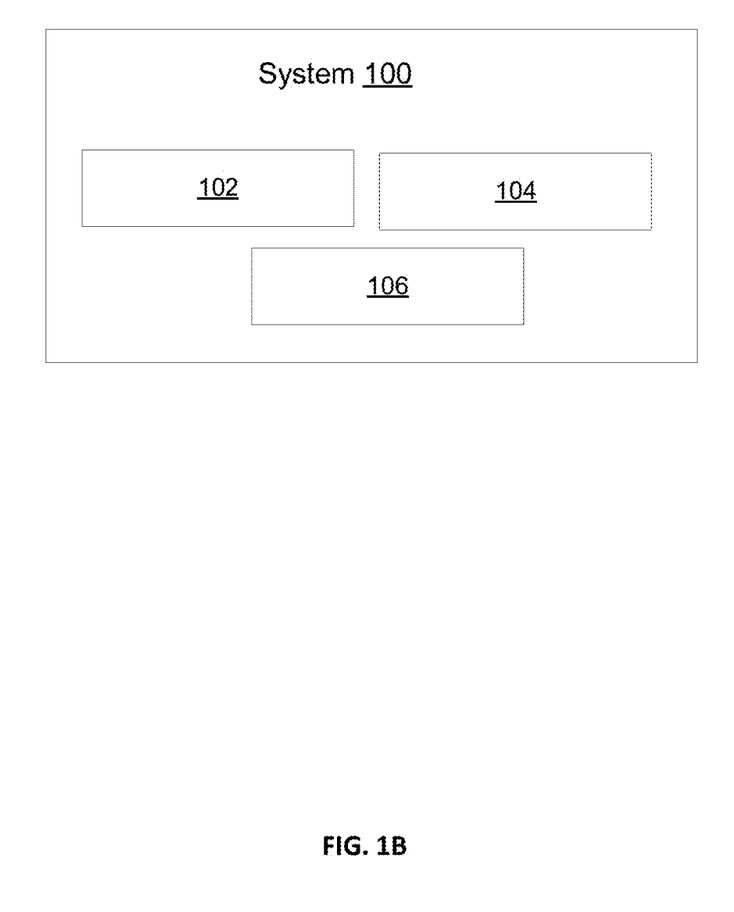
FIG. 1B is a diagram illustrating an exemplary environment in which some embodiments may operate.

FIG. 1B illustrates a block diagram of an example system 100 for various embodiments that includes at least a pose module 102, an AR representation module 104 and an AR emanation module 106.

The pose module 102 may perform functionality as illustrated in FIGS. 3, 4, 5, 6A and 6B ("FIGS. 2-6B"). The pose module 102 may determine pose data and pose data changes for various types of devices, objects and/or items.

The AR representation module 104 may perform functionality as illustrated in FIGS. 2-6B. The AR representation module 104 may generate AR representation of a beam or magnetic field.

The AR emanation module 106 may perform functionality as illustrated in FIGS. 2-6B. The AR emanation module 106 may generate an AR visualization of emanation of the beam throughout an AR display of medical data. The AR emanation module 106 may generate an AR visualization of emanation of a magnetic field throughout an AR display of medical data.

The system 100 may further includes one or more user devices 140 (such as one or more Augmented Reality headset devices) to display output, via a user interface generated by an application engine. An exemplary user device may include, for example, a spatial transformation module, a camera module, a physical landmark module, a user manipulation module and an augmented reality display module 118. It is understood that the user device(s) 140 may further include one or more of the modules 102, 104, 106 or respective portions of any respective module(s) may be distributed and implemented amongst a plurality of user devices 140 and one or more workstations.

Any module or component of the system 100 may have access to a 3D model of medical data 122 or may have one or more portions of the 3D model 122 stored locally. While the databases(s) 120 is displayed separately, the databases and information maintained in a database may be combined together or further separated in a manner the promotes retrieval and storage efficiency and/or data security.

According to various embodiments, a database(s) associated with the system 100 maintains information, such as 3D medical model data, in a manner the promotes retrieval and storage efficiency and/or data security. In addition, the 3D medical model data may include rendering parameters, such as data based on selections and modifications to a 3D virtual representation of a medical model rendered for a previous Augmented Reality display. In various embodiments, one or more rendering parameters may be preloaded as a default value for a rendering parameter in a newly initiated session of the system 100.

In one or more embodiments, an Augmented-Reality (AR) headset device may implement one or more modules of the Field Visualization Engine. A user may wear the AR headset device that generates and displays an AR display. The AR headset device tracks one or more poses (and changes in poses) of various items and/or object. In various embodiments, a camera(s) disposed on the AR headset device captures one or more images of the various items and/or object as the AR headset device's position and orientation changes due to user movements. In some embodiments, the AR headset device generates an AR display, a 3D virtual representation of a medical model ("3D virtual medical model"), and a 3D virtual representation of a body part of the user ("3D virtual hands").

In various embodiments, the Field Visualization Engine accesses one or more storage locations that contain respective portions of 3D medical model data. The 3D medical model data may include a plurality of slice layers of medical data associated with external and/or internal anatomies. For example, the 3D medical model data may include a plurality of slice layers of medical data for illustrating external and internal anatomical regions of a user's head, brain and skull, etc. It is understood that various embodiments may be directed to generating displays of any internal or external anatomical portions of the human body and/or animal bodies.

According to various embodiments, respective pose data of the AR headset device, a collimator, and a physical patient each represents a physical position and orientation in a 3D space defined by a unified coordinate system. In some embodiments, the AR headset device identifies respective coordinates for pose data relative to a predefined fixed reference point. In some embodiments, the collimator (or external instrument arm) and the patient may each have one or more fiducial markers tracked by the AR headset device. The respective pose data may be based on tracked positions and orientations of the fiducial markers. The Field Visualization Engine may further apply various types of spatial transformations to pose data.

As shown in flowchart 200 of FIG. 2, the Field Visualization Engine tracks one or more positions and orientations of a collimator ("collimator poses") relative to one or more positions and orientations of an Augmented Reality (AR) headset device ("headset poses" or "device poses") worn by a user. (Act 202) Each respective collimator pose and each respective headset pose corresponds to a three-dimensional (3D) unified coordinate space ("3D space").

The Field Visualization Engine generates an AR representation of a beam (such as a radiation beam) emanating from the collimator based at least on a current collimator pose and a current headset pose. The Field Visualization Engine further generates an AR visualization of emanation of the beam throughout an AR display of medical data. (Act 204). Various embodiments generate an AR representation of a simulated radiation beam and/or generate a real-time AR representation an actual radiation beam currently being delivered. Various embodiments generate an AR representation of a simulated magnetic field and/or a real-time AR representation of an actual magnetic field that is currently being generated. The Field Visualization Engine further generates an AR visualization of emanation of the beam throughout an AR display of medical data. (Act 206) In various embodiments, the AR visualization may be of emanation of a magnetic field.

Figure 3:
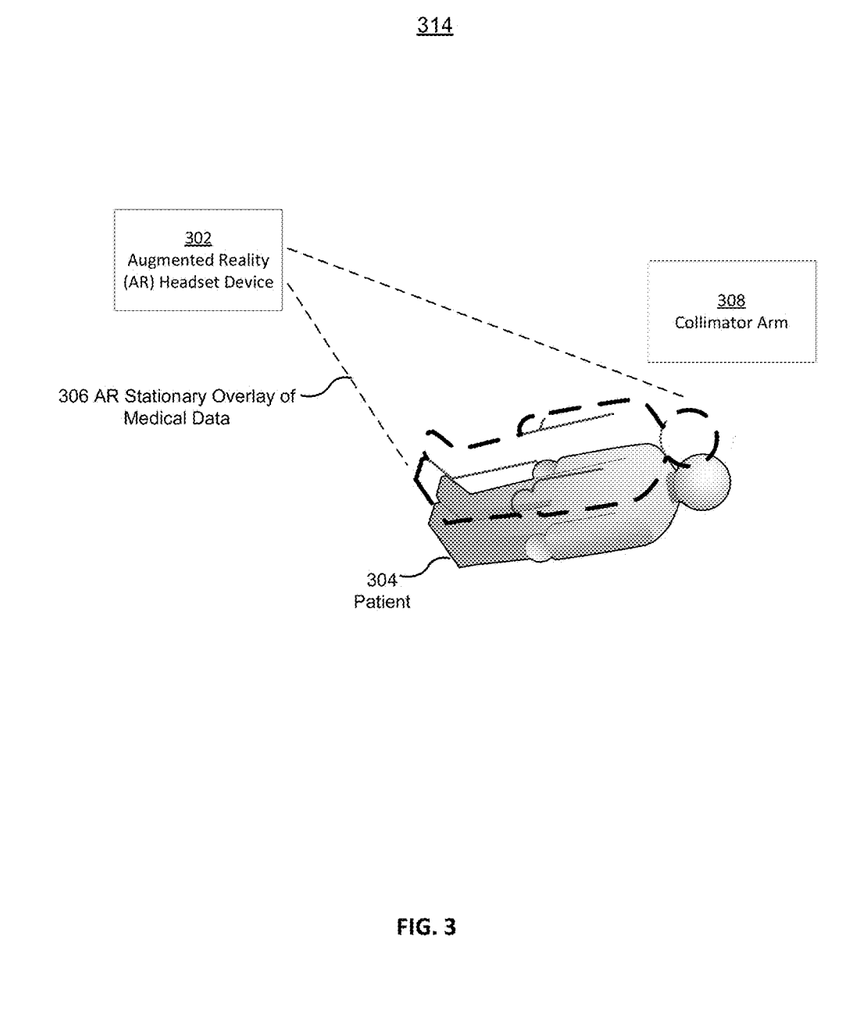
FIG. 3 is a diagram illustrating an exemplary environment in which some embodiments may operate.

In various embodiments, as shown in FIG. 3, the Field Visualization Engine generates an AR overlay of medical data 306. The AR headset device displays the overlay 306 in an AR display. The overlay 306 may be based on 3D medical model data representative of a portion of an internal anatomy of a patient 304. The patient may be position proximate to a collimator 308. The Field Visualization Engine determines a display position for the overlay 306 according to a position and orientation defined according to the 3D space such that the overlay 306 is displayed over a portion of the physical patient's body in alignment with the patient's internal anatomy. As the user moves around the patient, the Field Visualization Engine captures the current headset pose and retrieves medical model data that corresponds with the user's perspective view as represented by the headset pose as the user continually moves and the headset pose continually changes. The Field Visualization Engine updates the overlay 306 by rendering newly retrieved medical model data in the overlay 306.

Figure 4:
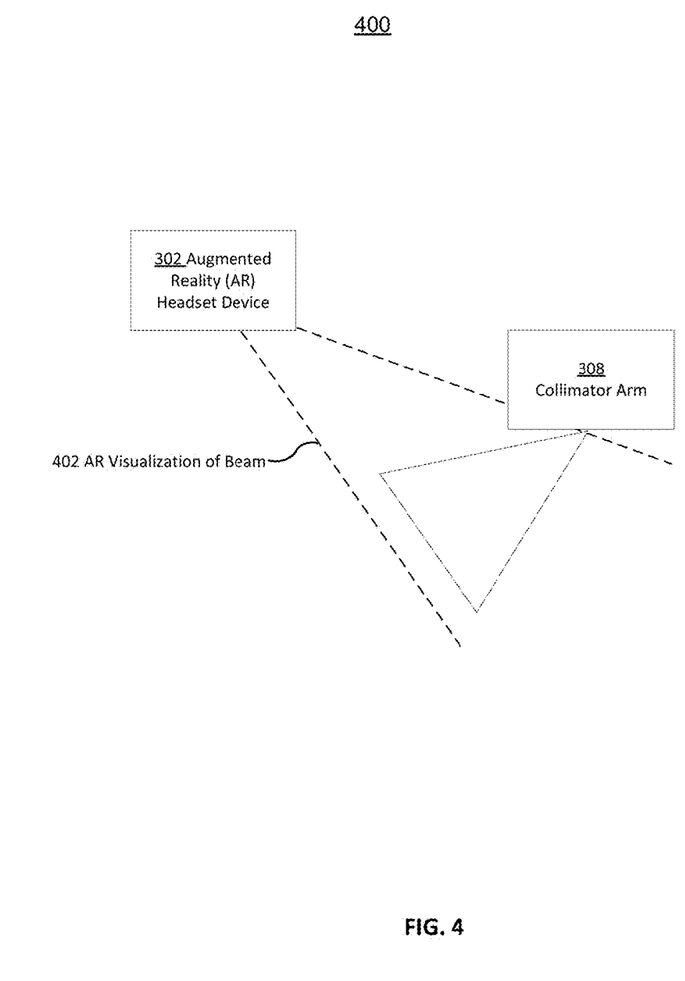
FIG. 4 is a diagram illustrating an exemplary environment in which some embodiments may operate.

In one or more embodiments, as shown in FIG. 4, the Field Visualization Engine determines a collimator pose for a collimator 308 physically positioned proximate to the patient 304. The AR headset further generates an AR visualization 402 of a simulated radiation beam targeted at the patient 304. It is understood that the Field Visualization Engine may utilize various types of parameters in generating the AR visualization 402 of a simulated radiation beam such as, for example, the distance between the collimator 308 and the patient 304, the patient's current position and orientation in the 3D space, an angle of the collimator and various power settings of the collimator. The AR headset device displays the AR visualization 402 of a simulated radiation beam relative to a current headset pose. The user is thereby provided a view of the simulated radiation beam from the user's current perspective view as the user moves and the headset pose continually changes.

Figure 5:
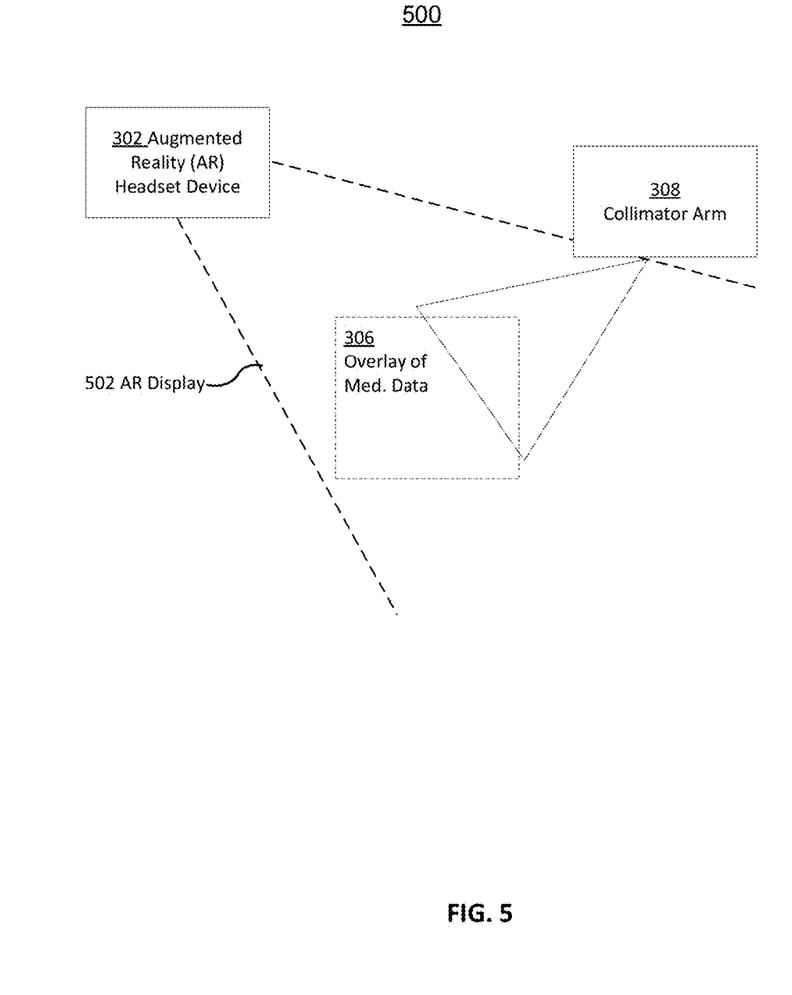
FIG. 5 is a diagram illustrating an exemplary environment in which some embodiments may operate.

According to one or more embodiments, as shown in FIG. 5, an AR display 502 generated by the AR headset device may further include concurrent display of the medical model data overlay 306 and the AR visualization 402 of a simulated radiation beam. Both the overlay 306 and the AR visualization 402 are generated by the AR headset device relative to headset pose(s), individually, to provide views of the overlay 306 and the AR visualization 402 from the user's perspective.

Figure 6A:
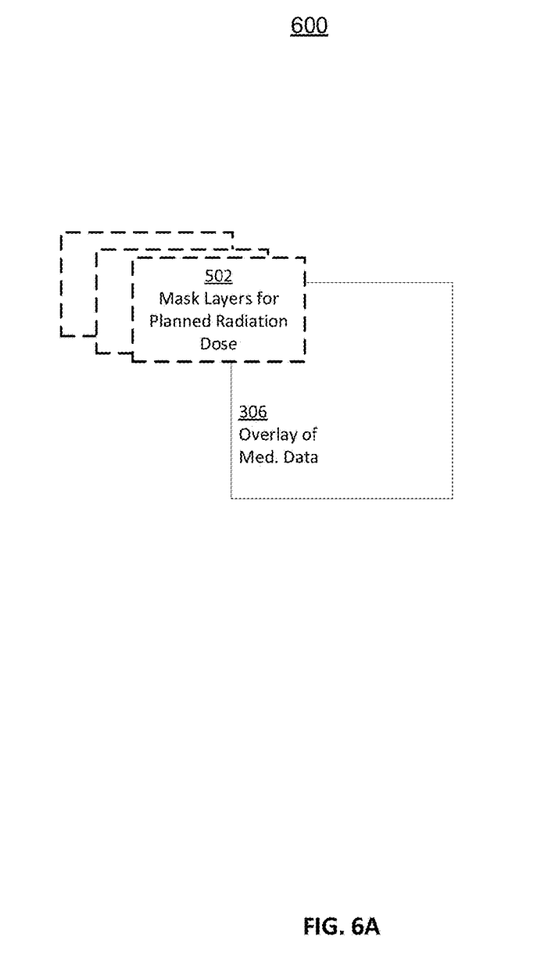
FIGS. 6A and 6B are each a diagram illustrating an exemplary environment in which some embodiments may operate.

In an embodiment(s), as shown in FIG. 6A, the Field Visualization Engine generates one or more mask layers 502 and incorporates the mask layers into the overlay 306. Each respective mask layer may represent a portion(s) of predicted emanation of a sphere of a planned radiation dose that is to be applied to the patient's internal anatomy. For example, a planned radiation dose may include an amount of radiation targeting a particular part of internal anatomy at a selected angle. As such, the mask layers provide a preview of how the sphere of the planned dose of radiation will emanate throughout the patient's internal anatomy and also provides a visual indication of predicted radiation fall off.

Figure 6B:
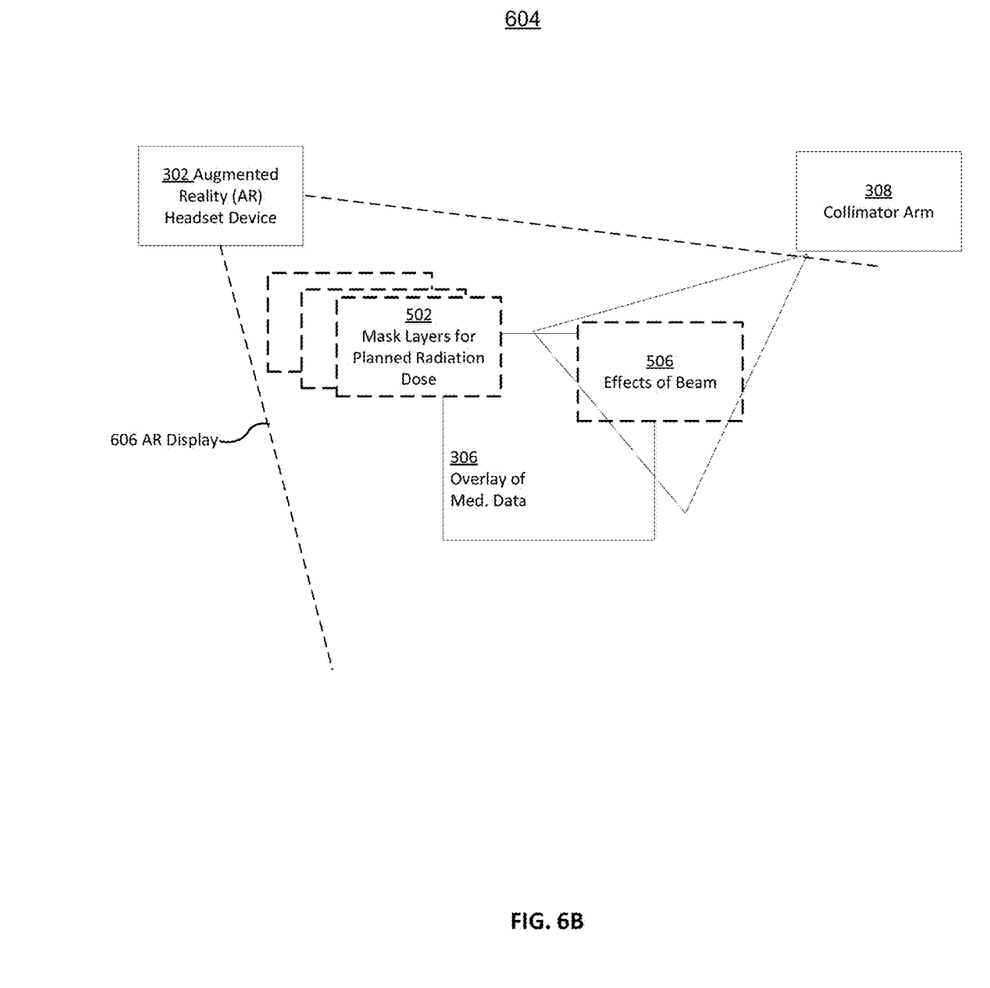

In various embodiments, as shown in FIG. 6B, the Field Visualization Engine may further determine predicted interactions between the simulated radiation beam and the various types of tissue, muscle and/or organs of the patient's internal anatomy represented by the medical model data. The AR headset device may generate an AR display 606 that incorporate visual indications in the overlay 306 to provide the user with a visualization of how the simulated radiation beam may emanate throughout the internal anatomy, the fall off of the simulated radiation beam and effects 506 the internal anatomy may experience as a consequence of exposure to the simulated radiation beam.

In some embodiments, the Field Visualization Engine may trigger display in the AR display 606 of a visual cue upon determining that the emanation of the simulated radiation beam that corresponds with the collimator's current pose and power settings meets a similarity threshold (or is in alignment) with respect to the emanation of the planned dose of radiation and its fall off as displayed in the overlay 306 according to the mask layers 502. As such, the visual cue informs the user that the collimator's current pose and power settings that correspond with the simulated radiation beam are optimal for actually delivering the planned radiation dose to the patient.

Figure 7:
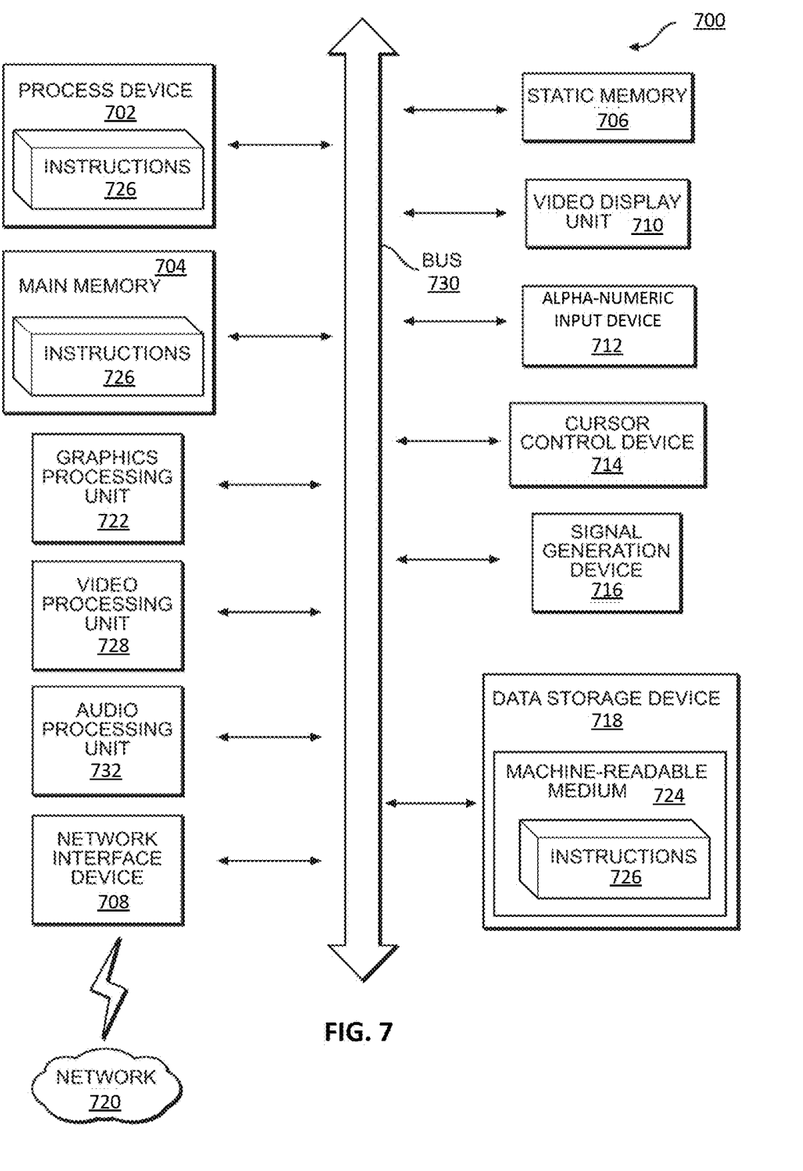
FIG. 7 is a diagram illustrating an exemplary environment in which some embodiments may operate.

FIG. 7 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 718, which communicate with each other via a bus 730.

Processing device 702 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute instructions 726 for performing the operations and steps discussed herein.

The computer system 700 may further include a network interface device 708 to communicate over the network 720. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), a graphics processing unit 722, a signal generation device 716 (e.g., a speaker), graphics processing unit 722, video processing unit 728, and audio processing unit 732.

The data storage device 718 may include a machine-readable storage medium 724 (also known as a computer-readable medium) on which is stored one or more sets of instructions or software 726 embodying any one or more of the methodologies or functions described herein. The instructions 726 may also reside, completely or at least partially, within the main memory 704 and/or within the processing device 702 during execution thereof by the computer system 700, the main memory 704 and the processing device 702 also constituting machine-readable storage media.

In one implementation, the instructions 726 include instructions to implement functionality corresponding to the components of a device to perform the disclosure herein. While the machine-readable storage medium 724 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:
   tracking one or more positions and orientations of a collimator ("collimator poses") relative to one or more positions and orientations of an Augmented Reality (AR) headset device ("headset poses"), each respective collimator pose and each respective headset pose corresponding to a three-dimensional (3D) unified coordinate space ("3D space");
   generating an AR representation of a beam emanating from the collimator based at least on a current collimator pose and a current headset pose;
   determining a current position and an orientation of a physical patient ("patient pose"), the patient pose corresponding to the 3D space; and
   generating an AR visualization of emanation of the beam throughout an AR display of medical data based, comprising:
      generating the AR display of the medical data as a visual overlay based at least on the patient pose and relative to the current headset pose, the medical data corresponding to one or more volumes for a portion of internal anatomy of the physical patient, wherein generating the AR display of the medical data comprises:
         generating one or more mask layers, each respective mask layer comprising a visual representation of at least a portion of a predicted emanation of a planned dose of radiation; and
         incorporating at least one of the mask layers into the AR display of medical data;
      determining whether an alignment exists between the predicted emanation of the planned dose of radiation and the AR visualization of emanation based on the current collimator and headset poses; and
      triggering a visual cue upon determining the alignment exists.

2. The computer-implemented method of claim 1, wherein generating an AR visualization of emanation of the beam throughout the AR display of medical data comprises:
   generating a visual representation of at least a portion of fall off of the beam; and
   incorporating display of the visual representation of the portion of fall off with the AR display of the medical data.

3. The computer-implemented method of claim 1, wherein generating an AR representation of a beam emanating from the collimator comprises:
   generating the AR representation of the beam further based at least on one or more collimator settings and an amount of distance between the collimator and a beam target.

4. The computer-implemented method of claim 3, wherein the beam target comprises a portion of internal anatomy of a physical patient.

5. A system comprising one or more processors, and a non-transitory computer-readable medium including one or more sequences of instructions that, when executed by the one or more processors, cause the system to perform operations comprising:
   tracking one or more positions and orientations of a collimator ("collimator poses") relative to one or more positions and orientations of an Augmented Reality (AR) headset device ("headset poses"), each respective collimator pose and each respective headset pose corresponding to a three-dimensional (3D) unified coordinate space ("3D space");

generating an AR representation of a beam emanating from the collimator based at least on a current collimator pose and a current headset pose;

determining a current position and an orientation of a physical patient ("patient pose"), the patient pose corresponding to the 3D space; and generating an AR visualization of emanation of the beam throughout an AR display of medical data, comprising:

generating the AR display of the medical data as a visual overlay based at least on the patient pose and relative to the current headset pose, the medical data corresponding to one or more volumes for a portion of internal anatomy of the physical patient, wherein generating the AR display of the medical data comprises:

generating one or more mask layers, each respective mask layer comprising a visual representation of at least a portion of a predicted emanation of a planned dose of radiation; and incorporating at least one of the mask layers into the AR display of medical data;

determining whether an alignment exists between the predicted emanation of the planned dose of radiation and the AR visualization of emanation based on the current collimator and headset poses; and triggering a visual cue upon determining the alignment exists.

6. The system of claim 5, wherein generating an AR visualization of emanation of the beam throughout the AR display of medical data comprises:

generating a visual representation of at least a portion of fall off of the beam; and incorporating display of the visual representation of the portion of fall off with the AR display of the medical data.

7. The system of claim 5, wherein generating an AR representation of a beam emanating from the collimator comprises:

generating the AR representation of the beam further based at least on one or more collimator settings and an amount of distance between the collimator and a beam target.

8. The system of claim 7, wherein the beam target comprises a portion of internal anatomy of a physical patient.

9. A computer program product comprising a non-transitory computer-readable medium having a computer-readable program code embodied therein to be executed by one or more processors, the program code including instructions for:

tracking one or more positions and orientations of a collimator ("collimator poses") relative to one or more positions and orientations of an Augmented Reality (AR) headset device ("headset poses"), each respective collimator pose and each respective headset pose corresponding to a three-dimensional (3D) unified coordinate space ("3D space");

generating an AR representation of a beam emanating from the collimator based at least on a current collimator pose and a current headset pose;

determining a current position and an orientation of a physical patient ("patient pose"), the patient pose corresponding to the 3D space; and generating an AR visualization of emanation of the beam throughout an AR display of medical data, comprising:

generating the AR display of the medical data as a visual overlay based at least on the patient pose and relative to the current headset pose, the medical data corresponding to one or more volumes for a portion of internal anatomy of the physical patient, wherein generating the AR display of the medical data comprises:

generating one or more mask layers, each respective mask layer comprising a visual representation of at least a portion of a predicted emanation of a planned dose of radiation; and incorporating at least one of the mask layers into the AR display of medical data;

determining whether an alignment exists between the predicted emanation of the planned dose of radiation and the AR visualization of emanation based on the current collimator and headset poses; and triggering a visual cue upon determining the alignment exists.

10. The computer program product of claim 9, wherein generating an AR visualization of emanation of the beam throughout the AR display of medical data comprises:

generating a visual representation of at least a portion of fall off of the beam; and incorporating display of the visual representation of the portion of fall off with the AR display of the medical data.

11. The computer program product of claim 9, wherein generating an AR representation of a beam emanating from the collimator comprises:

generating the AR representation of the beam further based at least on one or more collimator settings and an amount of distance between the collimator and a beam target.

* * * * *